(12) United States Patent
Ba-abbad

(10) Patent No.: US 9,127,243 B2
(45) Date of Patent: Sep. 8, 2015

(54) STIRRING APPARATUS FOR STIRRING MICROORGANISMS IN A CULTURING MEDIUM

(75) Inventor: Mazen A. Ba-abbad, Riyadh (SA)

(73) Assignee: King Abdulaziz City for Science and Technology (KACST), Riyadh (SA)

( * ) Notice: Subject to any disclaimer, the term of this patent is extended or adjusted under 35 U.S.C. 154(b) by 1193 days.

(21) Appl. No.: 12/954,599

(22) Filed: Nov. 24, 2010

(65) Prior Publication Data
US 2012/0129249 A1 May 24, 2012

(51) Int. Cl.
| C12M 1/00 | (2006.01) |
| B01F 7/00 | (2006.01) |
| B01F 7/16 | (2006.01) |
| B01F 7/18 | (2006.01) |
| B01F 13/00 | (2006.01) |
| B01F 15/00 | (2006.01) |
| C12M 1/06 | (2006.01) |

(52) U.S. Cl.
CPC ............ *C12M 21/02* (2013.01); *B01F 7/00116* (2013.01); *B01F 7/00141* (2013.01); *B01F 7/00291* (2013.01); *B01F 7/00975* (2013.01); *B01F 7/168* (2013.01); *B01F 7/18* (2013.01); *B01F 13/0049* (2013.01); *B01F 15/00454* (2013.01); *C12M 27/02* (2013.01)

(58) Field of Classification Search
CPC ...... C12M 23/18; C12M 23/56; C12M 27/07; B01F 7/243; B01F 13/0854; B01F 7/00; B01F 13/0827; C05F 17/0205; C05F 17/0258; C05F 17/027; C05F 17/02; C05F 17/0063; C12C 1/15; C12C 1/02; C12C 1/00

USPC ........................................................ 435/289.1
See application file for complete search history.

(56) References Cited

U.S. PATENT DOCUMENTS

| 3,548,770 | A | * | 12/1970 | Boutros | 261/91 |
| 4,482,510 | A | * | 11/1984 | Khudenko | 261/91 |
| 4,581,181 | A | * | 4/1986 | Nicholls | 261/91 |
| 4,681,711 | A | * | 7/1987 | Eaton | 261/91 |
| 2005/0061721 | A1 | * | 3/2005 | Tormaschy et al. | 210/121 |
| 2009/0232653 | A1 | * | 9/2009 | Vitale | 416/36 |

FOREIGN PATENT DOCUMENTS

EP    1394246    *    3/2004

OTHER PUBLICATIONS

EP1394246 English translation Mar. 2004.*

* cited by examiner

*Primary Examiner* — Nathan Bowers
*Assistant Examiner* — Timothy Barlow
(74) *Attorney, Agent, or Firm* — Timberline Patent Law Group PLLC

(57) ABSTRACT

The invention provides a stirring apparatus for stirring microorganisms such as, an alga in a culturing medium. The stirring apparatus includes one or more supporting structures. The stirring apparatus further includes a plurality of paddle units operatively connected to the one or more supporting structures. The plurality of paddle units are submerged in the culturing medium holding the microorganisms. Further, the plurality of paddle units are configured to rotate for stirring the microorganisms in the culturing medium. In response to the rotation of the plurality of paddle units, the stirring apparatus propels in the culturing medium.

19 Claims, 6 Drawing Sheets

STIRRING APPARATUS FOR STIRRING MICROORGANISMS IN A CULTURING MEDIUM

FIELD OF THE INVENTION

The present invention generally relates to stirring microorganisms in a culturing medium. More specifically, the invention relates to a stirring apparatus for stirring microorganisms such as, an alga in a culturing medium.

BACKGROUND OF THE INVENTION

Numerous methods and systems exist for cultivating microorganisms, for example, an alga. These methods include closed systems for cultivating the microorganisms. A typical closed system may be a tube-based system for holding the microorganisms along with a culturing medium. However, installation cost as well as operation cost of such tube-based systems are usually high. Further, these microorganisms may require continuous supply of sunlight for performing photosynthesis and nutrients for their growth. However, in case of tube-based systems, the sunlight may not be properly directed towards these microorganisms. Moreover, cultivation of the microorganisms involves stirring of microorganisms which is difficult to perform in such tube-based systems. Further, if the microorganisms are cultivated in a flat container such as, a flat plate bioreactor unit, efficient distribution of nutrients and sunlight to all the microorganisms present in the flat container still remains a challenge. For example, in a flat container, a large amount of microorganisms present in a bottom layer of the container may not receive enough amounts of sunlight and nutrients for their growth due to the presence of microorganisms in the upper layer of the container. Thus, the microorganisms may need to be continuously stirred for efficient distribution of nutrients and sunlight, which is manually cumbersome.

Therefore, there is a need for an apparatus for efficiently stirring the microorganisms in a culturing medium for their growth.

BRIEF DESCRIPTION OF THE FIGURES

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the invention.

Figure 1:
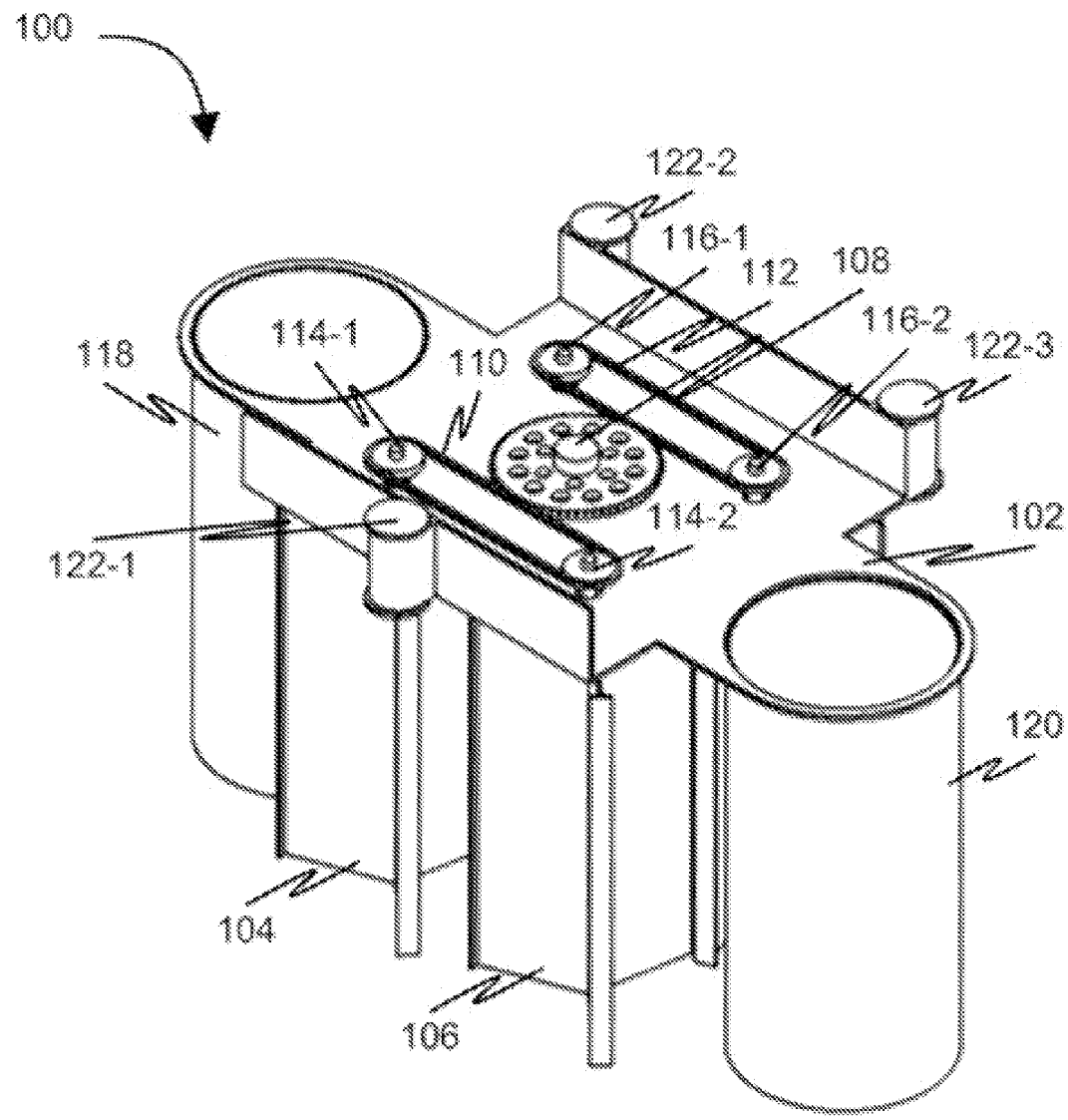
FIG. 1 illustrates a stirring apparatus for stirring microorganisms in a culturing medium in accordance with an embodiment of the invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the invention.

DETAILED DESCRIPTION OF THE INVENTION

Before describing in detail embodiments that are in accordance with the invention, it should be observed that the embodiments reside primarily in combinations of method steps and apparatus components related to method and system for stirring microorganisms in a culturing medium. Accordingly, the apparatus components and method steps have been represented where appropriate by conventional symbols in the drawings, showing only those specific details that are pertinent to understanding the embodiments of the invention so as not to obscure the disclosure with details that will be readily apparent to those of ordinary skill in the art having the benefit of the description herein.

Various embodiments of the invention provide a stirring apparatus for stirring microorganisms such as, an alga in a culturing medium. The stirring apparatus includes one or more supporting structures. The stirring apparatus further includes a plurality of paddle units operatively connected to the one or more supporting structures. The plurality of paddle units is submerged in the culturing medium holding the microorganisms. Further, the plurality of paddle units are configured to rotate for stirring the microorganisms in the culturing medium. In response to the rotation of the plurality of paddle units, the stirring apparatus propels in the culturing medium.

FIG. 1 illustrates a stirring apparatus for stirring microorganisms in a culturing medium in accordance with an embodiment of the invention. The stirring apparatus includes one or more supporting structures. The stirring apparatus further includes a plurality of paddle units operatively connected to the one or more supporting structures. The plurality of paddle units are submerged in the culturing medium holding the microorganisms. The microorganisms may include, but not limited to, alga. The culturing medium may include, but not limited to a liquid, a carbon dioxide gas, and nutrients for culturing the microorganisms. The liquid may be for example, but not limited to water. Further, the culturing medium containing the microorganisms and stirring apparatus may be maintained in an atmosphere having a temperature ranging from 24-27 deg Celsius. The atmosphere is maintained at a temperature range that facilitates the growth of the microorganisms. The temperature required for growth of the microorganisms may vary depending on a species of the microorganisms. The plurality of paddle units are configured to rotate for stirring the microorganisms in the culturing medium. The microorganisms are stirred in the culturing medium so that all the microorganisms obtain adequate amount of carbon dioxide and nutrients for their growth. In response to the rotation of the plurality of paddle units, the stirring apparatus propels in the culturing medium.

For ease of description and representation, a stirring apparatus 100 for stirring microorganisms in the culturing medium is shown to include a supporting structure 102 as shown in FIG. 1. However, a stirring apparatus such as, stirring apparatus 100 may include one or more supporting structures.

As shown in FIG. 1, stirring apparatus 100 further includes a paddle unit 104 and a paddle unit 106 coupled to supporting structure 102. Stirring apparatus 100 may include one or more paddle units in addition to paddle unit 104 and paddle unit 106. A paddle unit is explained in detail in conjunction with FIG. 2. Paddle unit 104 and paddle unit 106 are submerged in the culturing medium (not shown in FIG. 1) holding the microorganisms (not shown in FIG. 1). Paddle unit 104 and paddle unit 106 submerged in the culturing medium may be oriented substantially vertical to a horizontal plane. Further, paddle unit 104 and paddle unit 106 are configured to rotate for stirring the microorganisms in the culturing medium. In response to stirring the microorganisms, microorganisms present in a bottom layer or lower layers of the culturing medium migrates to an upper layer of the culturing medium. The microorganisms migrated from the bottom layer to the upper layer may receive adequate amount of nutrients and carbon dioxide for their growth. The mechanism of stirring the microorganisms is further explained in detail in conjunction with FIG. 3. Further, while stirring the microorganisms, the nutrients present in the culturing medium may be efficiently mixed in the culturing medium and the culturing medium may be aerated. The rotation of paddle unit 104 and paddle unit 106 is controlled by a driving unit (not shown in FIG. 1). The driving unit is operatively connected to paddle unit 104 and paddle unit 106 for controlling the rotation of paddle unit 104 and paddle unit 106.

The driving unit includes a motor (not shown in FIG. 1). In an embodiment, the driving unit may further include a driving gear 108 operatively coupled to the motor. Driving gear 108 is configured to rotate by the motor. The driving unit further includes a driving member 110 and a driving member 112 operatively coupled to driving gear 108. Driving member 110 and driving member 112 rotate when driving gear 108 rotates. In an embodiment, driving member 110 and driving member 112 may have a belt like structure. In this case, driving member 110 and driving member 112 may include a plurality of teeth that enable driving member 110 and driving member 112 to engage with driving gear 108. Thus, once driving gear 108 rotates, driving member 110 and driving member 112 also operate along with driving gear 108.

Further, in an embodiment, the driving unit may also include a driven member 114-1 and a driven member 114-2 operatively connected to driving member 110 as shown in FIG. 1. Similarly, the driving unit may include a driven member 116-1 and a driven member 116-2 operatively connected to driving member 112 as shown in FIG. 1. In an embodiment, a driven member rotates in response to rotation of a driving member. For example, driven member 114-1 and driven member 114-2 rotate in response to rotation of driving member 110. Similarly, driven member 116-1 and driven member 116-2 rotate in response to rotation of driving member 112. In an embodiment, the driven member such as, driven member 116-1 and driven member 116-2 may be a gear. In this case, a driving member may have a plurality of teeth that engages with the driven member for operating the driven member. For example, driving member 112 may have a plurality of teeth that engages with driven member 116-1 and driven member 116-2 having a gear like structure. Thus, when the driving member 112 operates, driven member 116-1 and driven member 116-2 also rotate. Alternatively, the driven member such as, driven member 116-1 and driven member 116-2 may be a rolling wheel. In this embodiment, a driving member may be a belt that may be mounted on the driven member. For example, driving member 112 may be a belt that is mounted on driven member 116-1 and driven member 116-2. In this case, driven member 116-1 and driven member 116-2 may be a rolling wheel. Thus, when the driving member 112 operates, driven member 116-1 and driven member 116-2 also rotate.

Driven member 114-1 and driven member 114-2 are operatively connected to paddle unit 104 and paddle unit 106, respectively. Therefore, in response to rotation of driven member 114-1 and driven member 114-2, paddle unit 104 and paddle unit 106 also rotate. More specifically, rotation of paddle unit 104 and paddle unit 106 is controlled by driven member 114-1 and driven member 114-2, respectively. Once paddle unit 104 and paddle unit 106 rotate, stirring apparatus 100 propels forward and backward in the culturing medium. Further, it may be noted that a driving unit used for rotating paddle units such as, paddle unit 104 and paddle unit 106 of a stirring apparatus may be a belt drive unit or any other driving unit known in the art.

Stirring apparatus 100 may be floating while propelling in the culturing medium. Stirring apparatus 100 may float in the culturing medium such that an upper portion of stirring apparatus 100 may be above the culturing medium. Thus, the driving unit of stirring apparatus 100 may be above a level of culturing medium. To enable stirring apparatus 100 to float in the culturing medium, stirring apparatus 100 includes a flow guide unit 118 and a flow guide unit 120 coupled to supporting structure 102. Flow guide unit 118 and flow guide unit 120 aid in floating of stirring apparatus 100. In an embodiment, a flow guide unit such as, flow guide unit 118 and flow guide unit 120, may have a shape for example, but not limited to, cylindrical, cuboidal, hemispherical, spherical, and conical. Further, in an embodiment, a flow guide unit such as, flow guide unit 118 and flow guide unit 120 may be hollow. Alternatively, the flow guide unit may be composed of a lightweight material that enables stirring apparatus 100 to float in the culturing medium. A flow guide unit is further explained in detail in conjunction with FIG. 3.

In an embodiment, stirring apparatus 100 may be placed in a container holding the microorganisms and the culturing medium. The container may be for example, a bioreactor unit. Thus, stirring apparatus 100 includes a plurality of guiding units 122-$n$ coupled to supporting structure 102. Plurality of guiding units 122-$n$ includes a guiding unit 122-1, a guiding unit 122-2, and a guiding unit 122-3 as shown in FIG. 1. Plurality of guiding units 122-$n$ are configured to guide the propulsion of stirring apparatus 100 in the container. Plurality of guiding units 122-$n$ may include, but are not limited to, a roller, a sliding unit, and a wheel. The mechanism of guiding the propulsion of a stirring apparatus such as, stirring apparatus 100 in the culturing medium is further explained in detail in conjunction with FIG. 5.

Figure 2:
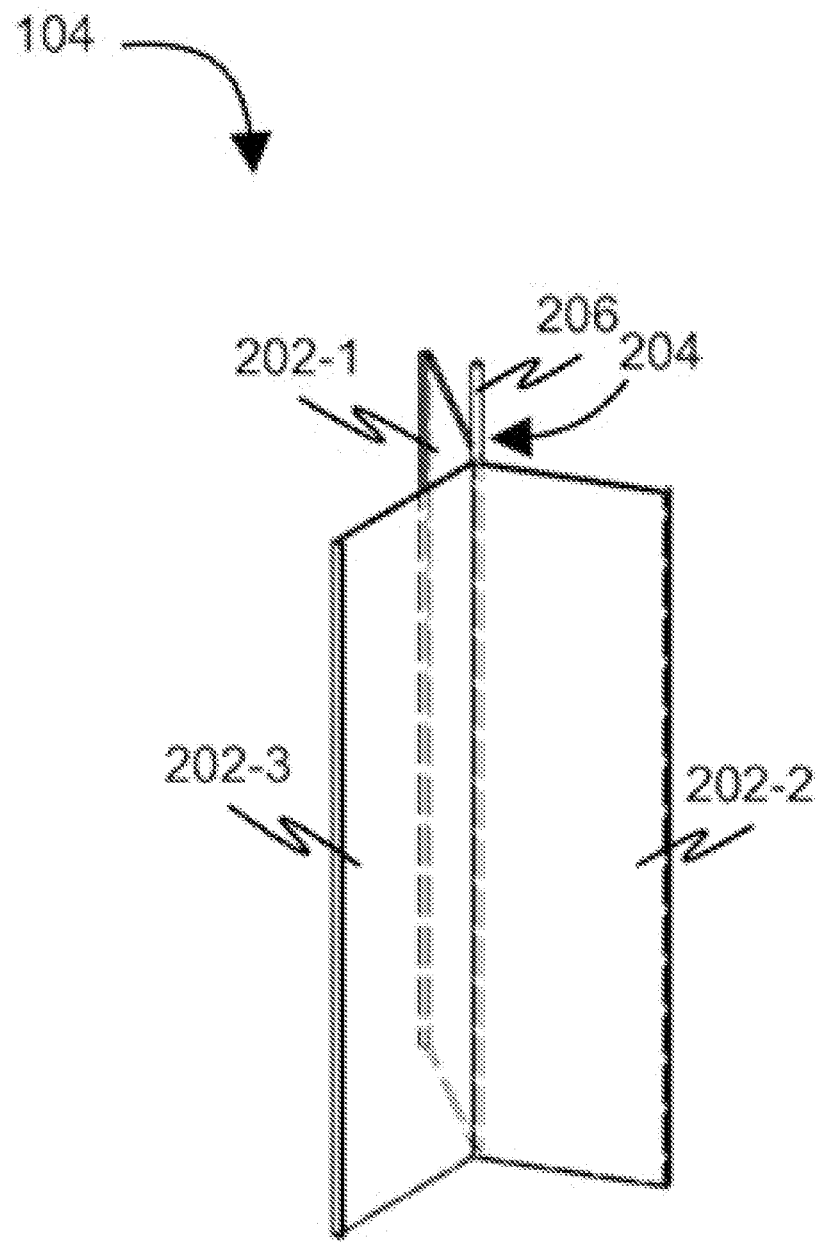
FIG. 2 illustrates a perspective view of a paddle unit of a stirring apparatus capable of stirring the microorganisms in the culturing medium in accordance with an embodiment of the invention.

FIG. 2 illustrates a perspective view of paddle unit 104 of a stirring apparatus capable of stirring the microorganisms in the culturing medium in accordance with an embodiment of the invention. As shown in FIG. 2, paddle unit 104 includes one or more paddle blades 202-$n$ connected to a shaft 204. The one or more paddle blades 202-$n$ include a paddle blade 202-1, a paddle blade 202-2, and a paddle blade 202-3. However, it will be apparent to a person skilled in the art that a paddle unit may include any number of paddle blades that enable the paddle unit for propelling the stirring apparatus. Shaft 204 of the paddle unit 104 may be connected to a driving unit of the stirring apparatus such as, stirring apparatus 100. More specifically, shaft 204 may be operatively connected to a driven member of the driving unit. For example, shaft 204 may have an end 206 operatively connected to driven member 114-1 of stirring apparatus 100. In this case, when driven member 114-1 starts operating, shaft 204 may rotate thereby rotating paddle unit 104. In an embodiment, the one or more paddle blades 202-n may extend substantially along a length of shaft 204.

Figure 3:
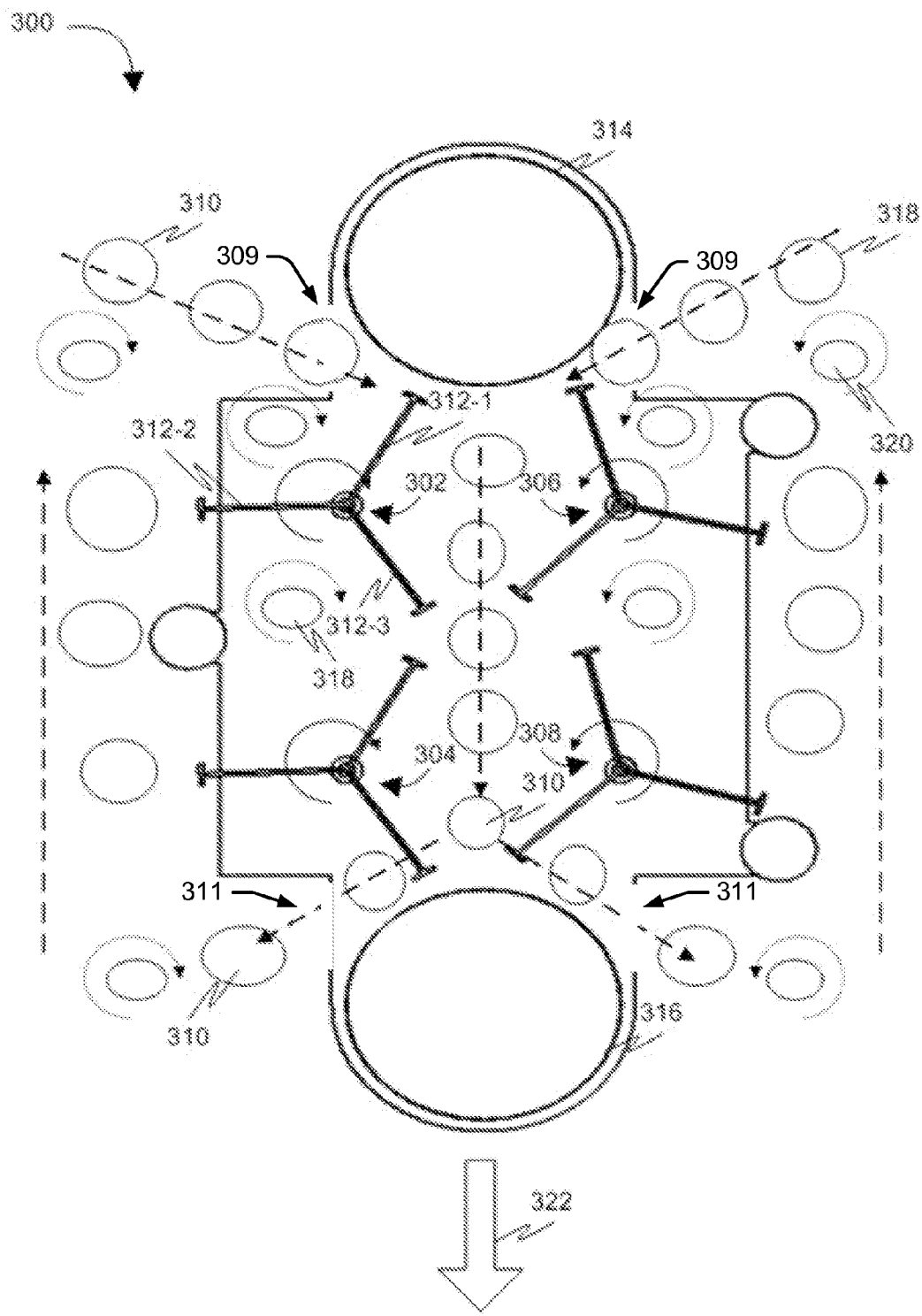
FIG. 3 illustrates a mechanism of stirring microorganisms in a culturing medium using the stirring apparatus in accordance with an embodiment of the invention.

FIG. 3 illustrates an exemplary stirring apparatus 300 for stirring microorganisms in a culturing medium in accordance with an embodiment of the invention. Stirring apparatus 300 may include a paddle unit 302, a paddle unit 304, a paddle unit 306 and a paddle unit 308. As shown in FIG. 3, paddle unit 302 and paddle unit 304 rotate in a clockwise direction. Similarly, paddle unit 306 and paddle unit 308 rotate in an anti-clockwise direction. The rotation of the paddle units is controlled by a driving unit as explained in detail in conjunction with FIG. 1. Upon rotation of paddle unit 302, a microorganism 310 along with the culturing medium is pulled inside stirring apparatus 300 through an inlet 309 of stirring apparatus 300. More specifically, microorganism 310 may be pulled between paddle unit 302 and paddle unit 306 as shown in FIG. 3. Microorganism 310 may also be pulled or pushed into stirring apparatus 300 by a plurality of paddle blades 312-n of paddle unit 302. Plurality of paddle blades 312-n may include a paddle blade 312-1, a paddle blade 312-2 and a paddle blade 312-3. For example, paddle blade 312-1 may push microorganism 310 within stirring apparatus 300 when microorganism 310 reaches near paddle blade 312-1. Microorganism 310 pulled inside stirring apparatus 300 through the inlet 309 may be guided by a flow guide unit 314 into stirring apparatus 300. In an embodiment, flow guide unit 314 may be cylindrical in shape to conveniently guide microorganism 310 towards the inlet 309 of stirring apparatus 300. However, flow guide unit 314 may have any other shape as explained in conjunction with FIG. 1. Microorganism 310 may be pulled along with the culturing medium within stirring apparatus 300. Once microorganism 310 reaches a vicinity of paddle unit 304, microorganism 310 is pushed out of stirring apparatus 300 through an outlet 311 of stirring machine 300. Microorganism 310 pushed outside of stirring apparatus 300 through the outlet 311 may be guided by a flow guide unit 316.

Similarly, upon rotation of paddle unit 306, a microorganism 318 along with the culturing medium is pulled inside stirring apparatus 300 through another inlet 309 of stirring apparatus 300. In this case, microorganism 318 pulled inside stirring apparatus 300 through the inlet 309 may be guided by flow guide unit 314. Further, microorganism 318 along with the culturing medium flows inside stirring apparatus 300 in response to rotation of paddle unit 306. Once microorganism 318 reaches a vicinity of paddle unit 308, microorganism 318 is pushed out of stirring apparatus 300 through another outlet 311 of stirring apparatus 300. Microorganism 318 pushed outside of stirring apparatus 300 through the outlet 311 may be guided by flow guide unit 316.

Moreover, when paddle unit 302, paddle unit 304, paddle unit 306, and paddle unit 308 rotates a vortex is created in the culturing medium. FIG. 3 illustrates paddle unit 302 and paddle unit 304 rotating in a clockwise direction and paddle unit 306 and paddle unit 308 rotating in an anti-clockwise direction to create the vortex force. The creation of the vortex reduces the pressure in a bottom layer of the culturing medium. Thus, a pressure difference may be created between the bottom layer and an upper layer in the culturing medium. Due to this pressure difference, microorganisms present in the bottom layer of the culturing medium may migrate to the upper layer of the culturing medium. For example, a microorganism 320 present in the bottom layer of the culturing medium may migrate to the upper layer of the culturing medium due to a vortex force experienced on microorganism 320. Microorganism 320 may rotate in a direction as illustrated in FIG. 3, when the vortex force is exerted on microorganism 320. Microorganism 320 may rotate in response to rotation of the culturing medium due to the vortex force. As a result, the rotation of paddle unit 302, paddle unit 304, paddle unit 306 and paddle unit 308 facilitates microorganisms present in the bottom layer to migrate to the upper layer thereby preventing settling of the microorganisms in the bottom layer. Further, due to creation of the vortex force, the microorganisms present in the culturing medium can circulate along the various layers of the culturing medium thereby receiving enough amounts of nutrients and carbon dioxide. Moreover, the nutrients and the carbon dioxide dissolved in culturing medium may be distributed among all the microorganisms present in the various layers.

Further, in response to rotation of paddle unit 302, paddle unit 304, paddle unit 306, and paddle unit 308, stirring apparatus 300 propels in a direction indicated by arrow 322 in the culturing medium. Paddle unit 302, paddle unit 304, paddle unit 306, and paddle unit 308 may rotate in a direction opposite to direction illustrated in FIG. 3 to enable stirring apparatus 300 to propel in a direction opposite to the direction indicated by arrow 322. Thus, stirring apparatus 300 may be capable of moving in a forward direction and a backward direction interchangeably.

Figure 4:
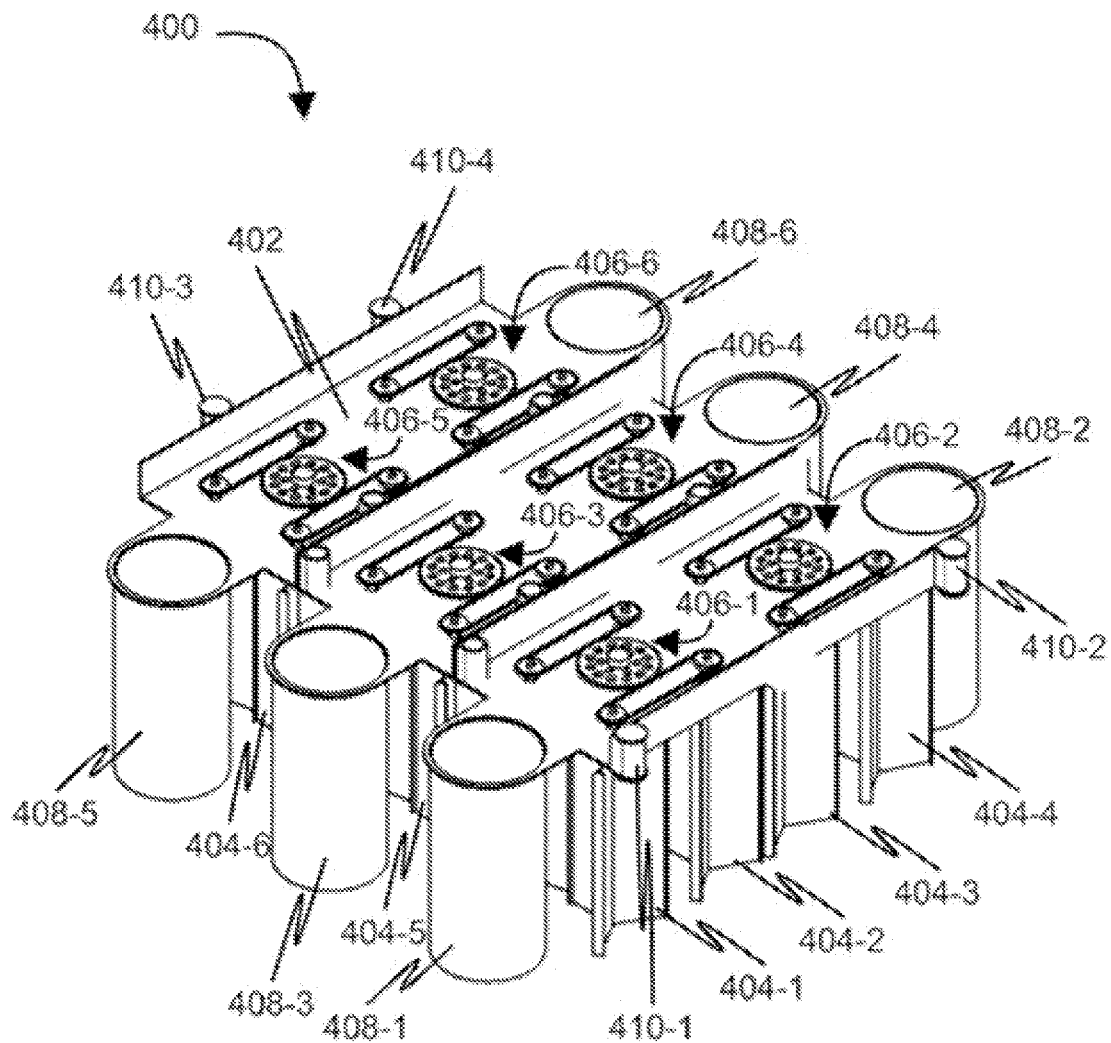
FIG. 4 illustrates a stirring apparatus for stirring microorganisms in a culturing medium in accordance with another embodiment of the invention.

Now referring to FIG. 4, wherein a stirring apparatus 400 for stirring microorganisms in a culturing medium in accordance with another embodiment of the invention is illustrated. Stirring apparatus 400 includes a supporting structure 402. However, it may be noted that stirring apparatus 400 may have more than one supporting structures and these supporting structures may be connected to each other. Stirring apparatus 400 further includes a plurality of paddle units 404-n coupled to supporting structure 402. A paddle unit is explained in detail in conjunction with FIG. 2. Plurality of paddle units 404-n include a paddle unit 404-1, a paddle unit 404-2, a paddle unit 404-3, a paddle unit 404-4, a paddle unit 404-5 and a paddle unit 404-6. Plurality of paddle units 404-n are submerged in the culturing medium (not shown in FIG. 4) holding the microorganisms (not shown in FIG. 4). Plurality of paddle units 404-n may be oriented substantially vertical to a horizontal plane.

Plurality of paddle units 404-n are operatively connected to one or more driving units 406-n. The mechanism of operation of a driving unit is explained in detail in conjunction with FIG. 1. One or more driving units 406-n include a driving unit 406-1, a driving unit 406-2, a driving unit 406-3, a driving unit 406-4, a driving unit 406-5, and a driving unit 406-6. Each driving unit of one or more driving units 406-n may be connected to four paddle units. However, it may be noted that the each driving unit may be connected to more than four paddle units. FIG. 4 does not illustrate all the paddle units connected to each driving unit for ease of representation of stirring apparatus 400. Thus, as shown in FIG. 4, paddle unit 404-1 and paddle unit 404-2 may be operatively connected to driving unit 406-1. Similarly, paddle unit 404-3 and paddle unit 404-4 may be operatively connected to driving unit 406-2. Further, paddle unit 404-5 and paddle unit 404-6 may be connected to driving unit 406-3 and driving unit 406-5, respectively. Further, plurality of paddle units 404-n are configured to rotate for stirring the microorganisms in the culturing medium. The rotation of plurality of paddle units 404-n is controlled by one or more driving units 406-n. The mechanism of operation of a paddle unit and the mechanism of connecting the paddle unit with a driving unit are explained in detail in conjunction with FIG. 2 and FIG. 3.

Stirring apparatus 400 further includes a plurality of flow guide units 408-*n* coupled to supporting structure 402. The plurality of flow guide units 408-*n* includes a flow guide unit 408-1, a flow guide unit 408-2, a flow guide unit 408-3, a flow guide unit 408-4, a flow guide unit 408-5, and a flow guide unit 408-6. The plurality of flow guide units 408-*n* aid in floating of stirring apparatus 400 in the culturing medium. A flow guide unit is further explained in detail in conjunction with FIG. 3. Stirring apparatus 400 may float in the culturing medium such that an upper portion of stirring apparatus 400 may be above the culturing medium. Thus, one or more driving units 406-*n* of stirring apparatus 400 may be above a level of culturing medium.

In addition, stirring apparatus 400 includes a plurality of guiding units 410-*n* coupled to supporting structure 402. Plurality of guiding units 410-*n* includes a guiding unit 410-1, a guiding unit 410-2, and a guiding unit 410-3, and guiding unit 410-4. Plurality of guiding units 410-*n* are configured to guide the propulsion of stirring apparatus 400 in the culturing medium. The mechanism of guiding the propulsion of stirring apparatus in the culturing medium is further explained in detail in conjunction with FIG. 5.

Figure 5:
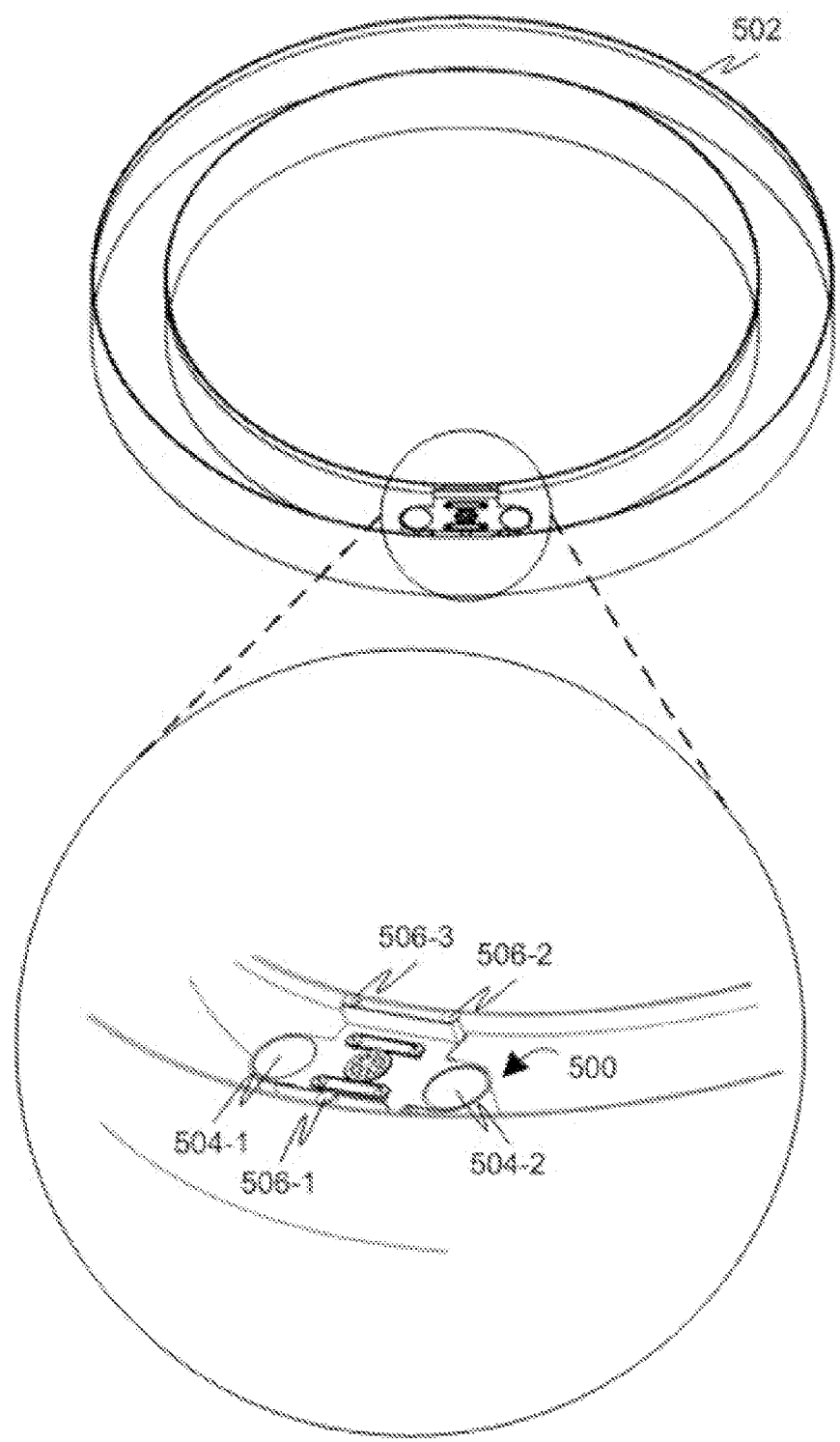
FIG. 5 illustrates a stirring apparatus placed in a bioreactor unit holding culturing medium and microorganisms in accordance with an embodiment of the invention.

A stirring apparatus is usually placed within a container such as, a bioreactor unit holding the microorganism and the culturing medium. FIG. 5 illustrates a stirring apparatus 500 placed in a bioreactor unit 502 holding the culturing medium and microorganisms in accordance with an embodiment of the invention. A stirring apparatus is further explained in detail in conjunction with FIG. 1. In an embodiment, bioreactor unit 502 may be a circular racetrack unit. However, bioreactor unit 502 may be for example, but not limited to an elliptical racetrack unit, a straight path unit, a cylindrical unit. Stirring apparatus 500 includes a plurality of paddle units (not shown in FIG. 5 for ease of representation) configured to rotate for stirring the microorganisms in the culturing medium. The rotation of the plurality of paddle units for stirring the microorganisms is explained in detail in conjunction with FIG. 3.

As a result of rotation of the plurality of paddle units, stirring apparatus 500 propels in bioreactor unit 502 holding the culturing medium and the microorganisms. The propulsion of stirring apparatus 500 in bioreactor unit 502 is assisted by a plurality of flow guide units 504-*n*. Plurality of flow guide units 504-*n* includes a flow guide unit 504-1 and a flow guide unit 504-2. The function of a flow guide unit is explained in detail in conjunction with FIG. 1 and FIG. 3. Further, the propulsion of stirring apparatus 500 in bioreactor unit 502 is guided by a plurality of guiding units 506-*n*. Plurality of guiding units 506-*n* includes a guiding unit 506-1, a guiding unit 506-2, and a guiding unit 506-3. Plurality of guiding units 506-*n* may contact walls of bioreactor unit 502 for guiding stirring apparatus 500 in bioreactor unit 502 while propelling. More specifically, plurality of guiding units 506-*n* may contact the wall of bioreactor unit 502 for example, a circular racetrack unit to guide stirring apparatus 500 to steadily follow the circular racetrack. Thus, plurality of guiding units 506-*n* provide stability to stirring apparatus 500 during propulsion. A guiding unit of plurality of guiding units 506-*n* may be for example, but not limited to a roller, a sliding unit, a wheel.

Figure 6:
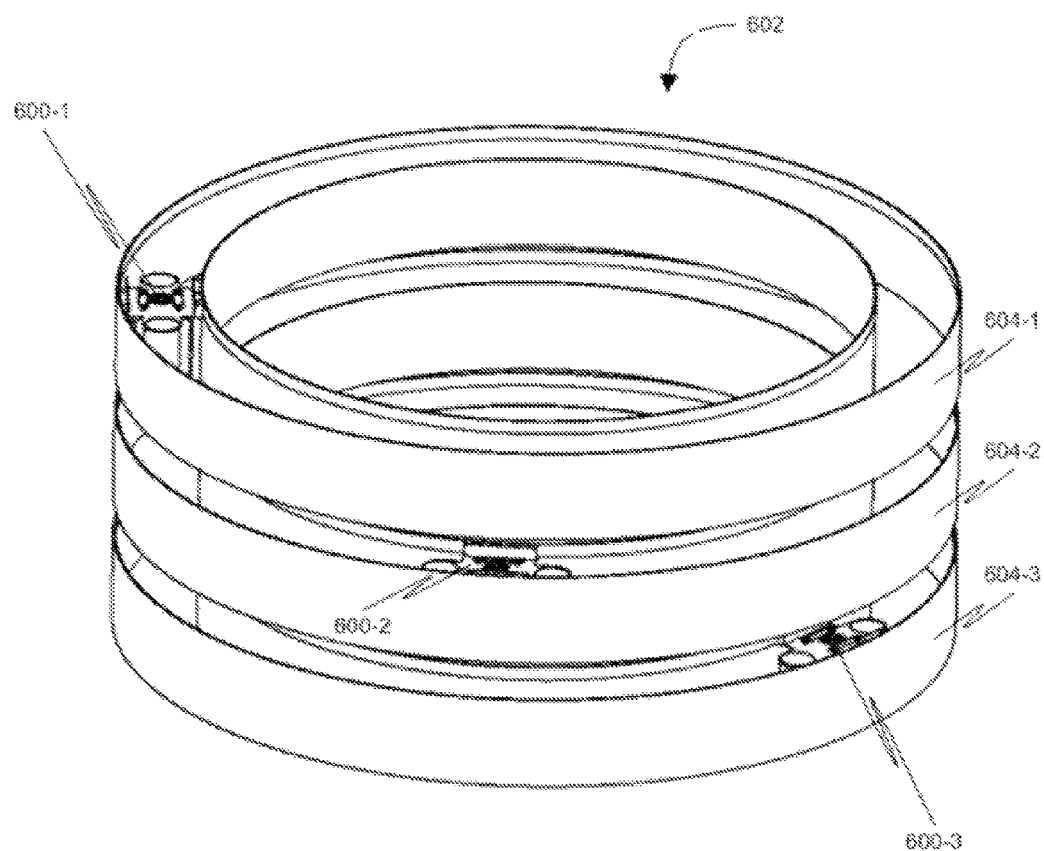
FIG. 6 illustrates a plurality of stirring apparatuses placed in a bioreactor unit holding culturing medium and microorganisms in accordance with another embodiment of the invention.

FIG. 6 illustrates a plurality of stirring apparatuses 600-*n* placed in a bioreactor unit 602 holding culturing medium and microorganisms in accordance with another embodiment of the invention. The plurality of stirring apparatuses 600-*n* includes a stirring apparatus 600-1, a stirring apparatus 600-2, and a stirring apparatus 600-3. A stirring apparatus is explained in detail in conjunction with FIG. 1. In an embodiment, bioreactor unit 602 may be a circular racetrack unit. However, bioreactor unit 502 may be for example, but not limited to an elliptical racetrack unit, a straight path unit, a cylindrical unit. Further, bioreactor unit 602 may includes a tray unit 604-1, a tray unit 604-2, and a tray unit 604-3. As shown in FIG. 6, stirring apparatus 600-1 may be placed in tray unit 604-1 holding culturing medium and microorganisms. Similarly, stirring apparatus 600-2 may be placed in tray unit 604-2 and stirring apparatus 600-3 may be placed in tray unit 604-3.

Each stirring apparatus of the plurality of stirring apparatuses 600-*n* includes a plurality of paddle units (not shown in FIG. 6 for ease of representation) configured to rotate for stirring microorganisms in the culturing medium. The rotation of the plurality of paddle units for stirring microorganisms is explained in detail in conjunction with FIG. 3. As a result of rotation of the plurality of paddle units, each stirring apparatus of the plurality of stirring apparatuses 600-*n* propels in bioreactor unit 602 holding the culturing medium. As shown in FIG. 6, stirring apparatus 600-1 propels in tray unit 604-1, stirring apparatus 600-2 propels in tray unit 604-2, and stirring apparatus 600-3 propels in tray unit 604-3. The propulsion of a stirring apparatus in a bioreactor unit is explained in detail in conjunction with FIG. 5.

Various embodiments of the invention provide a stirring apparatus for stirring microorganisms such as, an alga in a culturing medium. The stirring apparatus efficiently stirs the microorganisms in the culturing medium resulting in better mixing of nutrients. Further, the stirring apparatus enables the microorganisms present in a bottom layer of the culturing medium to migrate to an upper layer of the culturing medium resulting in a better reception of sunlight by the microorganisms. Thus, due to migration, these microorganisms can obtain enough amounts of nutrients and sunlight for their growth rather than settling in the bottom layer of the culturing medium. Moreover, stirring apparatus also eliminates the possibility of accumulation of microorganism in a certain layer or an area in the culturing medium. The stirring of the microorganism also results in efficient mixing of the nutrients in the culturing medium and aeration of the culturing medium. Further, the stirring apparatus is capable of self-propelling in the culturing medium while stirring the microorganisms. This self-propelling function enables the stirring apparatus to travel within a bioreactor unit holding the culturing medium and the microorganism and stir the microorganisms within the bioreactor unit. As a result, manual relocation of the stirring apparatus from one location to another location in the bioreactor unit for stirring the microorganisms may be avoided.

Those skilled in the art will realize that the above recognized advantages and other advantages described herein are merely exemplary and are not meant to be a complete rendering of all of the advantages of the various embodiments of the present invention.

In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of the present invention. The benefits, advantages, solutions to problems, and any element(s) that may cause any benefit, advantage, or solution to occur or become more pronounced are not to be construed as a critical, required, or essential features or elements of any or all the claims. The present invention is defined solely by the appended claims including any amendments made during the pendency of this application and all equivalents of those claims as issued.

What is claimed is:

1. A stirring apparatus for stirring microorganisms in a culturing medium, the stirring apparatus comprising:
   a plurality of circular troughs, each circular trough forming a continuous raceway ring and stacked on top of each other to form a stack of continuous raceway rings, each circular trough suitable for containing a bioreactor fluid comprising the culturing medium, each circular trough comprising:
   an open top for periodically exposing microorganisms to sunlight and nutrients;
   at least one floating supporting structure;
   a plurality of paddle units coupled to the at least one floating supporting structure and submerged in the culturing medium holding the microorganisms, wherein the plurality of paddle units are configured to rotate for stirring the microorganisms and to rotate for self-propelling the floating supporting structure along the continuous raceway ring;
   first guide units along a first side of the floating supporting structure disposed to stabilize the floating supporting structure with respect to an inside diameter of the circular trough during propulsion;
   second guide units along a second side of the floating supporting structure disposed to stabilize the floating supporting structure with respect to an outside diameter of the circular trough during propulsion;
   each paddle unit of the plurality of paddle units comprising a shaft having an end operatively connected to a driving unit and at least one paddle blade connected to the shaft, each paddle blade extending continuously along an axial length of each shaft to be submerged in the culturing medium; and
   at least one of the paddle units rotating in a clockwise direction and at least one of the paddle units rotating in an anti-clockwise direction and spaced to create at least one vortex to propel the microorganisms from a bottom layer to a top layer of the culturing medium while propelling the floating supporting structure along the continuous raceway ring.

2. The stirring apparatus of claim 1, wherein the plurality of paddle units are oriented vertically.

3. The stirring apparatus of claim 1, wherein the plurality of paddle units comprises at least one first paddle unit and at least one second paddle unit, wherein the at least one first paddle unit rotates in a direction opposite to direction of rotation of the at least one second paddle unit while stirring the microorganisms in the culturing medium.

4. The stirring apparatus of claim 3, wherein at least one first paddle unit and the at least one second paddle unit pulls the culturing medium holding the microorganisms through at least one inlet in the supporting structure in response to rotation of the at least one first paddle unit and the at least one second paddle unit.

5. The stirring apparatus of claim 4, wherein the at least one first paddle unit and the at least one second paddle unit pushes the culturing medium holding the microorganisms through at least one outlet in the supporting structure in response to rotation of the at least one first paddle unit and the at least one second paddle unit.

6. The stirring apparatus of claim 1, wherein the rotation of the plurality of paddle units in the culturing medium holding the microorganisms results in migration of the microorganisms present in a bottom layer of the culturing medium to an upper layer of the culturing medium.

7. The stirring apparatus of claim 1, wherein the microorganisms comprise an alga.

8. The stirring apparatus of claim 1 further comprising a plurality of flow guide units coupled to the supporting structure, wherein each flow guide unit of the plurality of flow guide units are configured to guide the culturing medium holding the microorganisms flowing into the supporting structure through at least one inlet in the supporting structure.

9. The stirring apparatus of claim 8, wherein the each flow guide unit of the plurality of flow guide units are further configured to guide the culturing medium holding the microorganisms flowing out of the supporting structure through at least one outlet in the supporting structure.

10. The stirring apparatus of claim 8, wherein the plurality of flow guide units aids floating of the floating supporting structure in the culturing medium.

11. The stirring apparatus of claim 8, wherein each flow guide unit of the plurality of flow guide units are shaped for assisting the floating supporting structure to self-propel in the culturing medium.

12. The stirring apparatus of claim 1 further comprising:
    at least one driving unit, a driving unit of the at least one driving unit is operatively connected to a paddle unit of the plurality of paddle units, wherein the at least one driving unit is configured to control the rotation of the plurality of paddle units.

13. The stirring apparatus of claim 12, wherein each driving unit of the at least one driving unit comprises:
    at least one motor;
    a driving gear coupled to the at least one motor, wherein the driving gear is configured to rotate;
    at least one driving member operatively coupled to the driving gear, the at least one driving member is driven by the driving gear in response to rotation of the driving gear; and
    at least one driven member operatively coupled to the at least one driving member, wherein a driven member of the at least one driven member is operatively connected to a paddle unit of the plurality of paddle units, the paddle unit rotates in response to driving the driven member by a driving member of the at least one driving member.

14. The stirring apparatus of claim 13, wherein a driven member of the at least one driven member is a gear.

15. The stirring apparatus of claim 1, wherein the floating supporting structure is placed in a bioreactor unit holding the culturing medium and the microorganisms.

16. The stirring apparatus of claim 15, wherein the bioreactor unit is at least one of a circular racetrack unit, an elliptical racetrack unit, and a straight path unit.

17. The stirring apparatus of claim 15 further comprising a plurality of guiding units connected to the floating supporting structure, wherein each guiding unit of the plurality of guiding units are configured to contact walls of the bioreactor unit for guiding the movement of the floating supporting structure in the bioreactor unit.

18. The stirring apparatus of claim 17, wherein a guiding unit of the plurality of guiding units comprises at least one of a roller, a sliding unit and a wheel.

19. The stirring apparatus of claim 1, wherein the floating support structure and the plurality of paddle units occupy a full cross-sectional area of the circular trough to thoroughly stir the microorganisms in a given cross-section of the circular trough as the floating support structure self-propels along the continuous raceway ring.

* * * * *